(12) United States Patent
Israel

(10) Patent No.: US 7,333,698 B2
(45) Date of Patent: Feb. 19, 2008

(54) OPTICAL SCANNING DEVICE

(75) Inventor: Henry M. Israel, Bnei Brak (IL)

(73) Assignee: Polyoptics Ltd, Shoham (IL)

(*) Notice: Subject to any disclaimer, the term of this patent is extended or adjusted under 35 U.S.C. 154(b) by 183 days.

(21) Appl. No.: 10/911,776

(22) Filed: Aug. 5, 2004

(65) Prior Publication Data
US 2006/0029341 A1  Feb. 9, 2006

(51) Int. Cl.
*G02B 6/04* (2006.01)

(52) U.S. Cl. ............ 385/115; 385/117; 385/118; 385/121; 385/120; 606/9; 607/88

(58) Field of Classification Search ............ 385/25, 385/115, 117, 118, 121, 120; 609/9; 607/88
See application file for complete search history.

(56) References Cited

U.S. PATENT DOCUMENTS

| | | | |
|---|---|---|---|
| 4,234,788 A * | 11/1980 | Palmer et al. | 250/227.26 |
| 4,617,926 A * | 10/1986 | Sutton | 606/9 |
| 5,059,192 A * | 10/1991 | Zaias | 606/9 |
| 5,269,779 A | 12/1993 | Sogawa et al. | |
| 5,321,501 A * | 6/1994 | Swanson et al. | 250/227.27 |
| 5,595,568 A * | 1/1997 | Anderson et al. | 606/9 |
| 6,168,590 B1 * | 1/2001 | Neev | 606/9 |
| 6,559,438 B1 | 5/2003 | Drobot et al. | |
| 6,632,218 B1 * | 10/2003 | Furumoto et al. | 606/9 |
| 6,738,539 B2 * | 5/2004 | Hagood et al. | 385/24 |
| 6,836,589 B2 * | 12/2004 | Sateeshchandra | 385/16 |

FOREIGN PATENT DOCUMENTS

| JP | 06339538 | 5/1993 |
|---|---|---|
| JP | 08299352 | 11/1996 |

* cited by examiner

*Primary Examiner*—Frank G. Font
*Assistant Examiner*—James P. Hughes
(74) *Attorney, Agent, or Firm*—The Nath Law Group; Jerald L. Meyer; Derek Richmond

(57) ABSTRACT

An optical scanning device including a bundle of optical fibers adapted for delivering optical energy beams therethrough, and an actuator coupled to the bundle of optical fibers adapted to bend the bundle of optical fibers in a scanning motion.

13 Claims, 1 Drawing Sheet

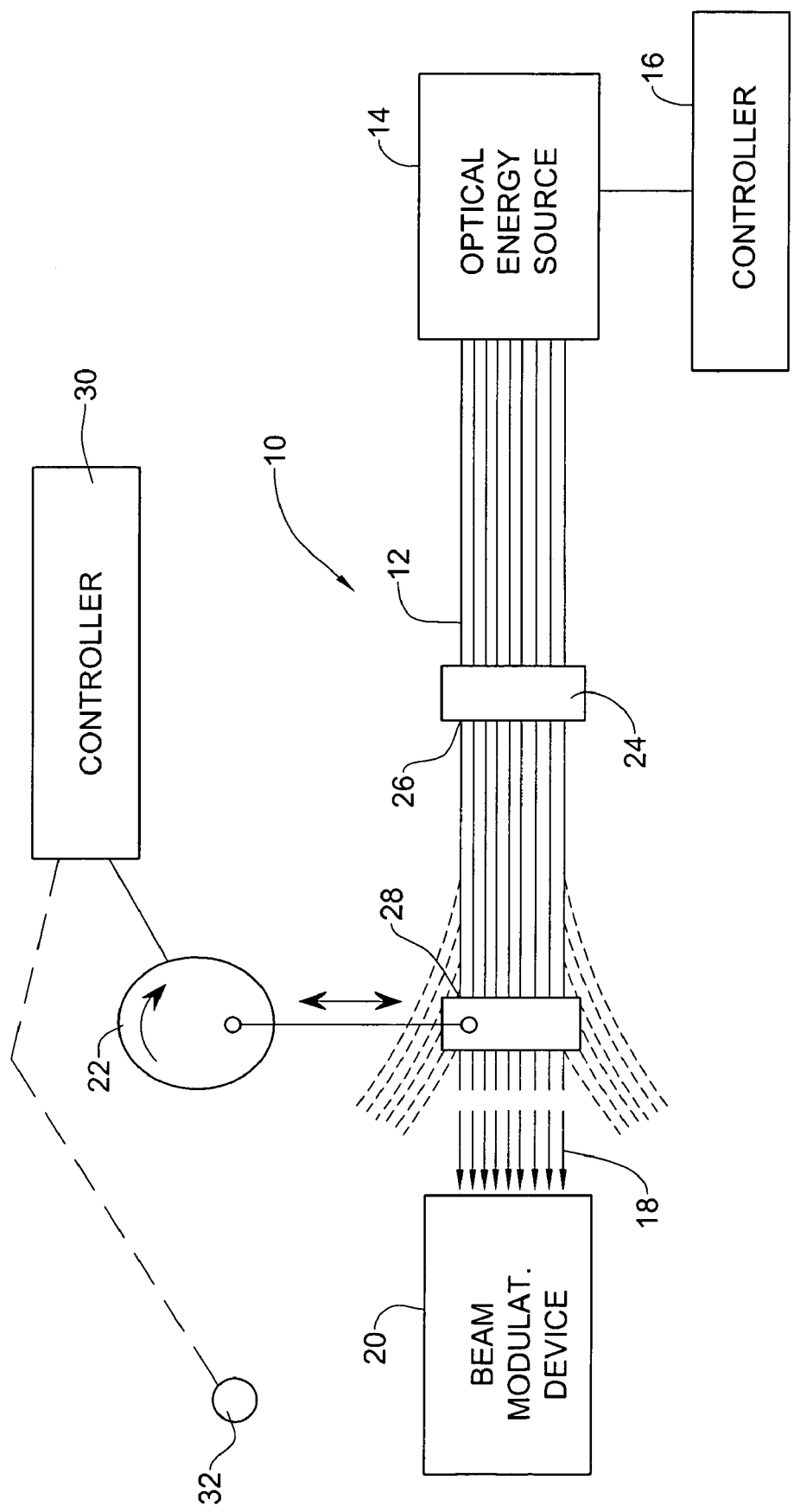

OPTICAL SCANNING DEVICE

FIELD OF THE INVENTION

The present invention relates generally to optical scanning devices, and particularly to an optical scanning device that scans by movement of a bendable and movable optical fiber bundle, particularly useful for, but not limited to, skin treatment and hair depilation.

BACKGROUND OF THE INVENTION

Laser devices have long been employed for skin ablation and/or hair removal and many other applications in the field of dermatology. For example, when the dermatological treatment is hair removal, it may be desired to heat and destroy a bulb of a hair follicle.

One of many examples of such laser devices is U.S. Pat. No. 6,511,475 to Altshuler et al., which describes methods and apparatus for dermatology treatment, such as for removal of unwanted hair, tattoos, port wine stains, spider veins or other vascular lesions, etc. The apparatus includes a handpiece that has three sections, an optical channel (i.e., a waveguide), a leading section which passes over the treatment area before the waveguide, and a trailing section which passes over the treatment area after the waveguide. Optical radiation is applied to the waveguide (or fiber bundle) or other suitable optical transmission components. Laser diodes or other suitable components may be in contact with the waveguide. The waveguide may be replaced with a lens or other suitable focusing or non-focusing optical transmission component (a waveguide, lens or other suitable focusing or non-focusing optical transmission component sometimes being collectively referred to hereinafter as an "optical channel"). The optical transmission component receives radiation from the radiation source utilized through a suitable optical transmission path.

Operation of the hair removal apparatus involves using continuous wave (CW) radiation, preheating the treatment volume, precooling, cooling during treatment and post-treatment cooling of the epidermis above the treatment volume, and various beam focusing techniques to reduce scattering and improve the delivery of the optical radiation.

The optical fiber bundles are stationary and are not part of the scanning apparatus.

U.S. Pat. No. 5,400,428 to Grace describes a method and apparatus for relatively moving energy across an array of optical fibers. The energy may be scanned across the fiber array. A dielectric mirror mounted on a galvanometer scanner is moved so as to cause successive pulses to irradiate different segments of the fiber optic array. As a result, each fiber receives radiation having sufficient flux while reducing the energy per pulse (or the CW equivalent). Rather than move the energy across the fiber array, the fiber array itself may be moved. One possible manner of movement is use of a piezo-electric stack.

It is important to note that although Grace contemplates moving the fiber array itself, the fiber array is moved as if it were a bundle of rigid sticks. In other words, the fibers are translated without any bending of individual fibers or groups of fibers.

SUMMARY OF THE INVENTION

The present invention seeks to provide a novel optical scanning device, as is described in detail further hereinbelow.

There is provided in accordance with an embodiment of the present invention an optical scanning device including a bundle of optical fibers adapted for delivering optical energy beams therethrough, and an actuator coupled to the bundle of optical fibers adapted to bend the bundle of optical fibers in a scanning motion.

The optical scanning device can include one or more of the following features. For example, an anchoring member may be attached to a first portion of the bundle of optical fibers, and the actuator may be attached to a second portion of the bundle of optical fibers and bend the second portion of the bundle of optical fibers in the scanning motion while the first portion of the bundle of optical fibers is held stationary by the anchoring member. The actuator may include a step motor, an oscillator and/or a solenoid, or any combination thereof. A sensor and a controller may be in operative communication with the actuator, the controller controlling operation of the actuator in accordance with information sensed by the sensor. A beam modulation device may be arranged relative to the bundle of optical fibers for modulating the optical energy beams. The bundle of optical fibers may be connected to a source of optical energy sufficient for performing a dermatological procedure.

The source of optical energy may include a coherent or non-coherent light source.

BRIEF DESCRIPTION OF THE DRAWINGS

The present invention will be understood and appreciated more fully from the following detailed description taken in conjunction with the drawing in which:

FIG. 1 is a simplified illustration of an optical scanning device, constructed and operative in accordance with an embodiment of the present invention.

DETAILED DESCRIPTION OF EMBODIMENTS

Reference is now made to FIG. 1, which illustrates an optical scanning device 10, constructed and operative in accordance with an embodiment of the present invention.

The optical scanning device 10 may include a bundle of optical fibers 12 connected to an optical energy source 14, capable of outputting sufficient energy for performing a dermatological procedure. For example, without limitation, optical energy source 14 may include a fiber coupled laser source, such as a laser diode, whose operation may be controlled by a controller 16. The laser diode may be tunable and may be provided with drivers and collimators as needed. Optical energy source 14 is not limited to coherent light and may include a source of non-coherent light (e.g., flash lamp) as well. The bundle of optical fibers 12 may include, without limitation, single mode or multi-mode fibers, which may or may not be doped (e.g., rare-earth doping).

The bundle of optical fibers 12 deliver optical energy beams 18 originating from source 14. A beam modulation device 20, such as but not limited to, a mirror or lens, may be arranged relative to the bundle of optical fibers 12 for modulating the optical energy beams 18.

An actuator 22 may be coupled to the bundle of optical fibers 12, which bends the bundle of optical fibers 12 in a scanning motion. In the non-limiting illustrated embodiment, an anchoring member 24 is attached to a first portion 26 of the bundle of optical fibers 12, and the actuator 22 is attached to a second portion 28 of the bundle of optical fibers 12. The actuator 22 bends the second portion 28 of the bundle of optical fibers 12 in the scanning motion while the first portion 26 of the bundle of optical fibers 12 is held stationary by the anchoring member 24. The anchoring member 24 may include, without limitation, a tie-down element, mechanical fastener and the like. The actuator 22 may include, without limitation, a step motor, an oscillator and/or a solenoid.

A controller 30 may be provided in operative communication with the actuator 22 and may cooperate with information sensed by a sensor 32 in a closed control loop to control operation of actuator 22. For example, the sensor 32 may be a temperature sensor (e.g., thermocouple or thermistor) which senses the temperature of the tissue being treated. The temperature may be used to increase or decrease the energy being delivered to the treatment site. The controller 30 may also operate in conjunction with a timer to control the oscillation and duration of the scanning. (Controller 16 may provide the functionality of controller 30, obviating the need for an extra controller. The controllers also ensure safety of the procedure.)

The optical scanning device 10 may be used to perform dermatological procedures, such as but not limited to, hair removal. For example, the source 14 of optical energy may be capable of delivering an energy flux of at least 20 $J/cm^2$, which is considered sufficient for hair removal. The optical energy may be adjusted (by the controller) in order to adjust the energy flux delivered to the treatment area. The energy flux equals the product of the power (of the optical beams) and the time duration. The time duration is a function of the scan rate. Therefore, by varying the scan rate (e.g., with the actuator 22 and controller 16) it is possible to vary the energy flux and arrive at optimal energy fluxes for the desired treatment.

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

What is claimed is:

1. An optical scanning device for performing a dermatological procedure comprising:
    a source of optical energy sufficient for performing the dermatological procedure;
    a bundle of optical fibers connected to the source of optical energy and adapted for delivering optical energy beams therethrough;
    an anchoring member attached to a first portion of said bundle of optical fibers; and
    an actuator coupled to a second portion of said bundle of optical fibers adapted to bend said bundle of optical fibers in a scanning motion while the first portion of said bundle of optical fibers is held stationary by said anchoring member.

2. The optical scanning device according to claim 1, wherein said actuator comprises at least one of a step motor, an oscillator and a solenoid.

3. The optical scanning device according to claim 1, further comprising a sensor and a controller in operative communication with said actuator, said controller controlling operation of said actuator in accordance with information sensed by said sensor.

4. The optical scanning device according to claim 1, further comprising a beam modulation device arranged relative to said bundle of optical fibers for modulating the optical energy beams.

5. The optical scanning device according to claim 4, wherein said beam modulation device comprises at least one of a mirror and a lens.

6. The optical scanning device according to claim 1, wherein said dermatological procedure comprises hair removal.

7. The optical scanning device according to claim 1, wherein said source of optical energy is capable of delivering an energy flux of at least 20 $J/cm^2$.

8. The optical scanning device according to claim 1, wherein said source of optical energy comprises a coherent light source.

9. The optical scanning device according to claim 1, wherein said source of optical energy comprises a non-coherent light source.

10. The optical scanning device according to claim 1, wherein said actuator is adapted to vary energy flux delivered by said bundle of optical fibers by varying a scan rate of said scanning motion.

11. An optical scanning device comprising:
    a bundle of optical fibers adapted for delivering optical energy beams therethrough and connected to a source of optical energy sufficient for performing hair removal and capable of delivering an energy flux of at least 20 $J/cm^2$;
    an anchoring member attached to a first portion of said bundle of optical fibers;
    an actuator attached to a second portion of said bundle of optical fibers and adapted to bend the second portion of said bundle of optical fibers in a scanning motion while the first portion of said bundle of optical fibers is held stationary by said anchoring member;
    a sensor and a controller in operative communication with said actuator, said controller controlling operation of said actuator in accordance with information sensed by said sensor; and
    a beam modulation device arranged relative to said bundle of optical fibers for modulating the optical energy beams.

12. The optical scanning device according to claim 1, wherein said bundle of said optical fibers has a width and a thickness, and wherein said optical fibers are placed one next to each other such that the width of the bundle is substantially greater than the thickness.

13. The optical scanning device according to claim 11, wherein said bundle of said optical fibers has a width and a thickness, and wherein said optical fibers are placed one next to each other such that the width of the bundle is substantially greater than the thickness.

* * * * *